US008987001B2

(12) United States Patent
Krueger et al.

(10) Patent No.: US 8,987,001 B2
(45) Date of Patent: Mar. 24, 2015

(54) OXYGEN INDICATOR FOR PARENTERAL AND ENTERAL DOSAGE FORMS

(75) Inventors: Volker Krueger, Nieste (DE); Rolf Beck, Melsungen (DE)

(73) Assignee: B. Braun Melsungen AG, Melsungen (DE)

( * ) Notice: Subject to any disclaimer, the term of this patent is extended or adjusted under 35 U.S.C. 154(b) by 421 days.

(21) Appl. No.: 13/376,848

(22) PCT Filed: Jun. 16, 2010

(86) PCT No.: PCT/EP2010/058441
§ 371 (c)(1),
(2), (4) Date: Dec. 8, 2011

(87) PCT Pub. No.: WO2010/146076
PCT Pub. Date: Dec. 23, 2010

(65) Prior Publication Data
US 2012/0083040 A1  Apr. 5, 2012

(30) Foreign Application Priority Data
Jun. 19, 2009  (EP) .................................. 09163218

(51) Int. Cl.
*G01N 31/22* (2006.01)
*G01N 21/78* (2006.01)

(52) U.S. Cl.
CPC .............. *G01N 31/225* (2013.01); *G01N 21/78* (2013.01)
USPC ........... 436/136; 422/420; 422/425; 436/166; 436/169

(58) Field of Classification Search
USPC .................... 436/136, 166, 169; 422/420, 425
See application file for complete search history.

(56) References Cited

U.S. PATENT DOCUMENTS

| 3,655,262 | A | * | 4/1972 | DePalma ....................... 359/453 |
| 3,856,528 | A | * | 12/1974 | Levinos ......................... 430/148 |
| 4,010,038 | A | * | 3/1977 | Iwasaki et al. ............. 106/31.24 |
| 4,062,799 | A | * | 12/1977 | Matsukawa et al. ........... 264/4.3 |
| 4,139,348 | A | * | 2/1979 | Swartz ............................. 436/35 |
| 4,169,811 | A | * | 10/1979 | Yoshikawa et al. ........... 436/138 |
| 4,328,181 | A | * | 5/1982 | Anders et al. ................. 422/425 |
| 4,349,509 | A | * | 9/1982 | Yoshikawa et al. ........... 422/426 |
| 4,526,752 | A | * | 7/1985 | Perlman et al. ............... 422/401 |
| 4,791,155 | A | * | 12/1988 | Gregory et al. .................. 524/22 |
| 5,096,813 | A | * | 3/1992 | Krumhar et al. ................ 435/28 |
| 5,206,118 | A | * | 4/1993 | Sidney et al. ................. 430/343 |
| 5,358,876 | A | * | 10/1994 | Inoue et al. .................... 436/136 |
| 6,093,572 | A | | 7/2000 | Stenholm et al. |
| 6,325,974 | B1 | * | 12/2001 | Ahvenainen et al. ......... 422/416 |
| 6,379,914 | B1 | * | 4/2002 | Pasco ............................... 435/25 |
| 6,399,387 | B1 | | 6/2002 | Stenholm et al. |
| 6,627,443 | B1 | | 9/2003 | Stenholm et al. |
| 6,676,901 | B1 | | 1/2004 | Hatakeyama et al. |
| 6,703,245 | B2 | * | 3/2004 | Sumitani et al. ............. 436/136 |
| 8,114,673 | B2 | * | 2/2012 | Mills et al. ....................... 436/77 |
| 2003/0082823 | A1 | * | 5/2003 | Sumitani et al. ............. 436/136 |
| 2004/0258562 | A1 | * | 12/2004 | Mills et al. ....................... 422/57 |
| 2006/0054526 | A1 | * | 3/2006 | Dean et al. .................. 206/459.1 |
| 2006/0223160 | A1 | * | 10/2006 | Vanzin ........................ 435/252.4 |
| 2007/0029527 | A1 | * | 2/2007 | Mills et al. ................... 252/408.1 |
| 2007/0031976 | A1 | | 2/2007 | Trouily et al. |
| 2007/0054412 | A1 | * | 3/2007 | Cregger et al. ............... 436/166 |

FOREIGN PATENT DOCUMENTS

| DE | 2812870 | | 9/1978 |
| EP | 0524021 B1 | | 9/1997 |
| EP | 1312918 A2 | | 5/2003 |
| EP | 0922219 B1 | | 4/2005 |
| JP | 55-43428 | * | 3/1980 |
| JP | 56-65072 | * | 6/1981 |
| JP | 5665072 | | 6/1981 |
| JP | 56-132560 | * | 10/1981 |
| JP | 56132560 | | 10/1981 |
| JP | 60-131459 | * | 7/1985 |
| JP | 63-187154 | * | 8/1988 |
| JP | 2006090773 A | | 4/2006 |
| WO | WO03021252 A1 | | 3/2003 |
| WO | WO2006135344 A1 | | 12/2006 |
| WO | WO2007018301 A1 | | 2/2007 |
| WO | WO2007059900 A1 | | 5/2007 |

OTHER PUBLICATIONS

Mills, A. et al, Chemical Communications 2005, 2721-2723.*

* cited by examiner

*Primary Examiner* — Arlen Soderquist
(74) *Attorney, Agent, or Firm* — Gregory N. Clements; Clements Bernard PLLC

(57) ABSTRACT

The present invention relates to an oxygen indicator in which the presence or absence of oxygen is made visible by a color change, and to the use of such oxygen indicator for monitoring parenteral and enteral dosage forms.

14 Claims, No Drawings

OXYGEN INDICATOR FOR PARENTERAL AND ENTERAL DOSAGE FORMS

The present invention relates to an oxygen indicator in which the presence or absence of oxygen is made visible by a color change, and to the use of such oxygen indicator for monitoring parenteral and enteral dosage forms.

In the medical field, many outer packagings of glass have been replaced by outer packagings of a plastic material. Plastic outer packagings are lighter in weight and often also less expensive. In the field of parenteral and enteral therapy, it is often necessary for the contents to be separated from ambient air, above all from oxygen. Plastic materials are more or less permeable for air and thus oxygen. By contact with oxygen, medical products may decompose and lose their activity, or undesirable degradation products may occur.

Therefore, it is necessary to check that no oxygen has penetrated to the air-sensitive product. Such proof should be performed quickly and simply, best without any auxiliaries.

In the prior art, indicators are known that change their color upon contact with oxygen. These are frequently metals or metal compounds, especially iron(II) compounds. Thus, EP 0 922 219 B1 and U.S. Pat. No. 6,093,572 A describe a colored composition consisting of a pyrogallol compound, an iron(II) salt and an organic acid. The pyrogallol compound is naturally or synthetically or semisynthetically produced tannin. In the presence of oxygen, the originally yellow composition turns black. The color change is based on oxidation of iron(II) to iron(III), which then reacts with the aromatic system of tannin.

U.S. Pat. No. 6,627,443 B1 and U.S. Pat. No. 6,399,387 B1 also describe a color composition consisting of an iron(II) compound and a pyrogallol compound. The color change of the oxygen indicator described herein can be reversed by reduction of the iron ions.

WO 2007/059900 A1 relates to an oxygen scavenger/indicator containing at least one oxygen sorbent consisting of a metal or a metal compound that can be converted to a higher oxidation state by oxygen. In addition, a complexing agent or redox indicator for the sorbent and an electrolyte are further contained. The indicator effect is caused by a change of the physical properties of the oxygen sorbent triggered by complex formation and/or interaction with the redox indicator.

JP 56132560 describes an oxygen-detecting composition. This composition is easily handled and exhibits a clear color difference in response to the presence or absence of oxygen. Such a material contains a compound with an oxazine nucleus, an iron compound, magnesium silicates and water or alcohol. The mixture turns red purple in the presence of oxygen, and white in the absence of oxygen. The change in hue is reversible.

In addition to metal ions, redox dyes are also employed as oxygen indicators. Several dyes are known that have a different color in their reduced form, or leuco or dihydro form, as compared to their oxidized form. A distinction is made between two-color indicators, such as ferroin (blue to red color transition) and one-color indicators, such as neutral red (colorless to red). The color change is reversible in all cases.

Thus, US 2007/0031976 A1 relates to an oxygen indicator that indicates the presence of oxygen within a packaging containing a medical composition. The indicator consists of a composition whose individual components are deemed safe for use with medical products. Indigo carmine serves as the redox dye and is mixed with cellulose, a reducing agent and water at a pH of 9.0 to 9.75.

JP 56065072 describes an oxygen-detecting compound. A compound with an oxazine skeleton serves as the redox dye. In addition, the composition includes glucose, at least one compound selected from a hydroxide, a silicate of an alkali or alkaline earth metal and aluminum hydroxide. The color change between the oxidized and reduced forms is reversible.

EP 0 524 021 B1 relates to an oxygen indicator containing at least one organic compound with three or more carbon atoms and at least one primary amino group and at least one hydroxy group, and at least one dye selected from the group consisting of thiazine dyestuffs, indigo dyestuffs and mixtures thereof. Further, at least one organic or inorganic acid is additionally contained. This patent specification relates to an oxygen indicator that indicates the presence or absence of oxygen in a gas phase intended to protect foodstuffs, electronic parts, electrical products having electronic parts, metallic parts or products having metallic parts.

The oxygen indicator of EP 1 312 918 A2 contains sheet silicates, cationic surfactants, an organic dye, a reducing agent and optionally a basic compound. By a reversible color change, the composition allows the presence or absence of oxygen or the concentration of oxygen to be checked.

U.S. Pat. No. 6,676,901 B1 relates to an oxygen indicator comprising an oxygen-indicating agent including a substrate and an oxygen indicator composition fixed at the surface of the substrate. In addition, this specification relates to a package binding oxygen and having an oxygen-indicating function, to which the oxygen indicator can be adhered. The specification further relates to a method and apparatus for fixing the oxygen indicator to an object.

Thus, it is the object of the present invention to provide a light- and heat-resistant oxygen indicator in which a color change is visually perceptible. The color change should proceed swiftly, but not within a few seconds. If the indicator is employed in a packaging, it should be possible for some minutes, even after the packaging has been opened, to recognize whether or not the indicator was in contact with oxygen before the packaging was opened. Further, the indicator should be designed in such a way that the oxygen-sensitive product remains visible. In particular, a preferably oxygen indicator is a redox dye that is colorless in the reduced state, and has an intensive color in the oxidized state, so that the presence of oxygen is clearly perceptible with the naked eye.

Surprisingly, the above object is achieved by a mixture of resorufin, methylene blue and/or toluidine blue as organic redox dye, one or more polyols, especially glycerol, and water, incorporated into one or more auxiliary agents. By the use of the polyol, water is bound in the oxygen indicator. In a preferred embodiment, the thus defined oxygen indicator additionally contains an organic or inorganic buffer, especially a phosphate and/or citrate buffer.

According to the invention, a 1 M buffer solution is preferably employed, so that a concentration of from 0.001 to 2 mol, especially from 0.01 to 1 mol, based on the oxygen indicator, is obtained.

If the oxygen indicator contains resorufin as the organic redox dye, the pH is adjusted within a range of from 6 to 10, preferably from 7 to 9, more preferably from 7.5 to 8.5. If methylene blue and/or toluidine blue is used as the redox dye, the pH is adjusted within a range of from 2 to 6, preferably from 3 to 5, more preferably from 3.5 to 4.5.

According to the invention, the oxygen indicator is preferably incorporated into an auxiliary agent. As possible auxiliary agents, methylcellulose, microcrystalline cellulose, lysine, lysine hydrochloride, magnesium stearate and/or silicones, especially gelatin and/or hydroxyethyl starches (HES), are employed. Gelatin and/or HES have a slightly reducing effect, so that the redox dye can be employed in its oxidized form and reduced just before being used as oxygen indicator.

HES may be used with different molecular sizes. An oxygen indicator according to the invention may be prepared with HES 130, but also with HES 200 and/or HES 450. The number describes the molar mass of the corresponding hydroxyethyl starch in kilodaltons.

Further, an oxygen indicator according to the invention can be applied to a support material, especially an ion exchanger, paper or sheet. In a preferred embodiment, an anion or cation exchanger based on a polymer or made of a polymeric carbohydrate derivative is used. Such an ion exchanger is first rinsed with a buffer, followed by applying the oxygen indicator. The use of an ion exchanger as a support material enables the pH to be adjusted by the ion exchanger itself, whereby a further addition of buffer is no longer necessary.

An oxygen indicator according to the invention may be in the form of a tablet, capsule or gel. These may in turn be placed into a separate outer packaging, preferably a bag or blister pack. By the thickness of the material of which the outer packaging consists, the oxygen permeability can be controlled and adjusted in accordance with the use.

Basically, there are three different variants of incorporating the dye:
1. The dye is reduced to the leuco or dihydro compound and further processed under inert gas.
2. The indicator is stabilized in the reduced form using protecting groups and incorporated in this form. The activation is effected in the final product by cleaving off the protecting group before, during or after heat treatment of the final product.
3. The indicator substance is incorporated in the oxidized form. The activation is effected in the final product by reduction before, during or after heat treatment of the final product.

If the redox dye is incorporated in the reduced form, all further process steps must be performed under inert gas in an oxygen-free atmosphere. Suitable for the reduction of the dye are reducing agents having a higher reduction potential than that of the corresponding dye itself, especially glucose, sodium disulfite, zinc, manganese(II) chloride; N-acetylcysteine and/or ascorbic acid. The reducing agents are separated off before the reduced dye is used as an oxygen indicator.

Protecting groups may be introduced to stabilize the reduced form of the redox dye. They are cleaved off in a temperature treatment. Preferably, a benzyl group is used for this purpose.

If the redox dye is incorporated in its oxidized form, the further treatment can be done under normal conditions. Reduction of the dye is then performed during a temperature treatment, for example, sterilization.

The dye may be immobilized by application to support materials or in corporation into auxiliary agents. The oxygen indicator may be applied as insignia on sheet or paper. Such insignia is not or hardly visible in the absence of oxygen. However, if the indicator should come into contact with oxygen, the insignia becomes visible. Thus, a confusion of colors is avoided.

According to the invention, the finished oxygen indicator may consist of small material-filled bags, for example, in a sachet shape. Another variant is to fill a blister pack or a punched or deep-drawn sheet in which the oxygen indicator can develop its color upon oxidation. The oxygen permeability of the outer packaging can be matched to needs. The oxygen permeability can be influenced by the thickness of a sheet employed.

In another embodiment, the oxygen indicator is used in the form of tablets or capsules. The coat of the capsule is preferably transparent. Preferably, it is a gel-filled capsule in which the oxygen indicator has been introduced into gelatin or HES.

An oxygen indicator according to the invention can be used for monitoring parenteral and enteral dosage forms, especially in the space between a bag for parenteral and enteral nutrition and a surrounding bag.

When resorufin is used as a redox dye, the color change is from colorless to red-purple in an oxygen indicator according to the invention. In the oxidation of methylene blue and/or toluidine blue, the originally colorless oxygen indicator turns blue. The hue can be varied by changing the concentration of the auxiliary agents, especially gelatin and/or hydroxyethyl starches. In the case of methylene blue and/or toluidine blue, there is a color change to green or purple, for example, by oxidation for high gelatin concentrations. In the reduced form, such an oxygen indicator is slightly yellow. Both forms are clearly discernible in color with the naked eye.

According to the invention, an oxygen indicator according to the invention can be used in the space between a bag for parenteral and enteral nutrition and a surrounding bag. In addition, an oxygen absorber can be employed in this space. It will bind any free oxygen and thus both increase the keeping quality of the parenteral and enteral dosage form and prolong the activity of the oxygen indicator.

In the following Examples, the indicator according to the invention will be illustrated, but not described in any exclusive way.

EXAMPLES

From the redox dyes, the following solutions were prepared:

Resorufin was dissolved in distilled water at a concentration of 1%. If necessary, the solution was diluted with distilled water. The corresponding concentrations are stated in the respective Examples.

Methylene blue was dissolved in distilled water at a concentration of 1%.

Toluidine blue was dissolved in distilled water at a concentration of 1%.

These were employed in the following Examples.

Example 1

Ion Exchanger Amberlite® CG-50 I

Three spatula-tipfuls each of ion exchanger CG-50 I was washed with WFI (water for injection), and the supernatant solution was decanted. Subsequently, the ion exchanger was admixed with 1% methylene blue solution, 1% toluidine blue solution or 0.001% resorufin solution and stirred. The mixture was allowed to stand for some time and stirred from time to time. Then, each mixture was filtered by means of a Büchner funnel with in-laid filter paper. The ion exchanger while still wet was subsequently filled into vials and sealed.

Of each ion-exchanger/indicator mixture, a spatula-tipful was filled into a surrounding bag and thermally sealed with an absorber bag. After a period of 14 days, all oxygen indicators were still colorless.

Example 2

Ten grams of a Dowex® 1-X8 ion exchanger was three times slurried with WFI and subsequently filtered in a suction filter. On top of the ion exchanger, a layer of 50 g of a 0.001% resorufin solution with a pH of 8 was placed. The mixture was stirred up several times and subsequently suction-filtered. The ion exchanger was then slurried with WFI and suction-filtered three more times.

The ion exchanger loaded with resorufin was transferred into a sample bottle.

Example 3

In another experiment, 10 g of gelatin was stirred with 40 g of WFI and 5 ml of a 1 M potassium phosphate buffer solution (pH 8.0) and allowed to swell for 20 minutes. Subsequently, 60 g of glycerol was added, mixed and heated at 65° C. in a water bath. Two grams of the resorufin-loaded ion exchanger Dowex® 1-X8 was added and stirred. The solution was transferred into a 250 ml infusion bottle and sterilized at 121° C. for 15 minutes.

Even after the sterilization, the ion exchanger remained mixed with the gelatin.

Example 4

A DEAE Sephadex® ion exchanger was swollen with WFI and admixed with 0.001% resorufin solution. The mixture was filtered through a suction filter, and the mixture was washed with a phosphate buffer at a pH of 8. The mixture was rinsed several times with resorufin solution to increase the concentration of resorufin. The intensively pink colored residue was transferred into vials and sealed. Of the mixture, 6 samples were thermally sealed into bags of Excel sheet, and each bag was placed into a 250 ml infusion glass bottle together with a Mitsubishi absorber bag. The bottles were sterilized at 121° C. for 15 minutes. After the sterilization, the color was maintained. Due to the oxygen absorber, the mixture becomes colorless.

After a period of three months, three infusion bottles in each of which one Excel bag with the DEAE Sephadex®/resorufin mixture was contained were opened. The Excel bag was opened slightly, and the mixture turned purple immediately.

In addition, another infusion bottle was opened in which a bead of DEAE Sephadex® ion exchanger loaded with resorufin and buffer at a pH of 8 were present over the same period. In addition, the mixture contained about 40% glycerol. Upon contact with oxygen, the bead turned intensively pink within 5 minutes.

Example 5

TABLE 1

|  | Gelatin | WFI | Citrate buffer pH 4 | Glycerol | Indicator |
|---|---|---|---|---|---|
| Exp. 5.1 | 20 g | 180 g | 10 g | 10 g | 100 μl 1% MB solution |
| Exp. 5.2 | 20 g | 180 g | 10 g | 10 g | 50 μl 1% TB solution |
| Exp. 5.3 | 40 g | 180 g | 10 g | 10 g | 100 μl 1% MB solution |

MB solution = methylene blue solution
TB solution = toluidine blue solution

The gelatin was mixed with WFI and citrate buffer and allowed to swell for 20 min. Thereafter, glycerol was added, and all was heated at about 65° C. in a water bath. Subsequently, the indicator was added, followed by mixing and removing from the water bath for cooling. Before gelling, the solutions were respectively filled into two 100 ml infusion bottles, capped and flanged. One bottle each was sterilized at 121° C. for 10 min, the other bottle was allowed to stand at room temperature.

Of each combination, pea-sized pieces were placed each into three 100 ml infusion bottles, provided with an oxygen absorber, and the bottles were sealed with a rubber stopper.

Example 6

TABLE 2

|  | Gelatin | WFI | 1M buffer | Glycerol | Indicator |
|---|---|---|---|---|---|
| Exp. 6.1 | 20 g | 100 g | 20 ml (pH 8) | 60 g | 0.24 g of 1% resorufin solution |
| Exp. 6.2 | 20 g | 100 g | 20 ml (pH 4) | 60 g | 0.595 g of 1% MB solution |
| Exp. 6.3 | 20 g | 100 g | 20 ml (pH 4) | 60 g | 0.51 g of 1% TB solution |

MB solution = methylene blue solution
TB solution = toluidine blue solution

In a thin plastic mortar, the gelatin, WFI and buffer solution were allowed to swell for 20 min. Then, glycerol was added, and the mixture was heated in a water bath at about 65° C. After the gelatin had dissolved, the indicator was added dropwise until the desired intensity of color was reached. The containers with the indicator were weighed before and after, and the difference was the consumption of indicator solution.

1 ml of each combination was filled into 6 Excel bags and thermally sealed. Each bag was placed into a 100 ml infusion bottle with an oxygen absorber, flushed with argon and sealed. Three bottles each of a combination were sterilized at 121° C. for 15 min, and the other 3 bottles were stored at room temperature.

Example 7

TABLE 3

|  | HES 200 | WFI | 1M buffer | Glycerol | Indicator |
|---|---|---|---|---|---|
| Exp. 7.1 | 75 g | 15 g | 15 ml (pH 8) | 45 g | 0.128 g of 1% resorufin solution |
| Exp. 7.2 | 75 g | 15 g | 15 ml (pH 4) | 45 g | 0.38 g of 1% MB solution |
| Exp. 7.3 | 75 g | 15 g | 15 ml (pH 4) | 45 g | 0.34 g of 1% TB solution |

MB solution = methylene blue solution
TB solution = toluidine blue solution

HES 200 was mixed with the buffer solution, WFI and glycerol. Subsequently, each combination was heated at about 80° C. in a water bath, and stirred. After a homogeneous mass had formed, the indicator was added dropwise until the desired color was reached. The containers with the indicator were weighed before and after, and the difference was the consumption of the respective indicator. Of each combination, one spatula spoonful was filled into 6 Excel bags and thermally sealed. Each bag was placed into a 100 ml infusion bottle with an oxygen absorber, flushed with argon and sealed. Three bottles each of a combination were sterilized at 121° C. for 15 min, and the other 3 bottles were stored at room temperature.

Example 8

TABLE 4

| HES 200 | 350 g |
|---|---|
| Lysine-HCl | 3 g |
| WFI | 70 g |
| Glycerol | 210 g |

The starch was mixed with lysine-hydrochloride, WFI and glycerol, and heated at about 80° C. in a water bath, and stirred until a homogeneous mass had formed. The temperature was kept constant for about 2 hours, followed by cooling down to room temperature and allowing to stand over night.

The mixture while still cold was divided into three beakers, and indicator solution was added.

TABLE 5

|  | HES-lysine mixture | Indicator |
|---|---|---|
| Exp. 8.1 | 113.543 g | 64 mg of 1% resorufin solution |
| Exp. 8.2 | 110.462 g | 169 mg of 1% MB solution |
| Exp. 8.3 | 109.817 g | 151 mg of 1% TB solution |

MB solution = methylene blue solution
TB solution = toluidine blue solution

All 3 beakers were heated at about 80° C. in a water bath, and the mixtures were liquefied. Then, the indicator was added until the desired color was reached.

Of each combination, one spatula spoonful was filled into 6 Excel bags and thermally sealed. Each bag was placed into a 100 ml infusion bottle with an oxygen absorber, flushed with argon and sealed. Three bottles each of a combination were heated (sterilized) at 121° C. for 15 min, and the other 3 bottles were stored at room temperature.

Example 9

From each combination of Examples 6, 7 and 8, one bag of the heat-treated variant of each indicator combination was removed from the bottle. The bags of the gelatin combinations turned the respective color after about 30 min. The bag of the HES combinations turned the respective color only after several hours.

Example 10

In order to test the possibility of reusing the oxygen indicator according to the invention, of the combinations from Examples 6, 7 and 8, an already heat-treated bottle and a not yet heat-treated bottle of each indicator combination were again heated (sterilized) at 121° C. for 15 min.

The bottles heat-treated the day before were also opened, the bags were removed, placed on a white surface, and of all samples, the changes were noted at predetermined intervals.

The results can be seen from the following Table 6.

TABLE 6

| | | Time (hours) | | | | | |
|---|---|---|---|---|---|---|---|
| Combination | immediately | 0.5 | 1 | 2 | 7 | 24 | |
| Exp. 6.1; one heat treatment | light yellow | purple | consistently purple | purple even more intensively | no more change | no more change | |
| Exp. 6.1; two heat treatments | light yellow | purple outside, yellow inside | consistently purple | purple even more intensively | no more change | no more change | |
| Exp. 6.2; one heat treatment | light yellow-light green | yellow inside, light green outside | consistently blue | no more change | no more change | no more change | |
| Exp. 6.2; two heat treatments | light yellow-light green | yellow inside, light green outside | consistently blue | no more change | no more change | no more change | |
| Exp. 6.3; one heat treatment | light yellow | yellow inside, light green outside | consistently blue | blue darker than with exp. 6.2 | no more change | no more change | |
| Exp. 6.3; two heat treatments | light yellow | yellow inside, light green outside | consistently blue | blue darker than with exp. 6.2 | no more change | no more change | |
| Exp. 7.1; one heat treatment | yellow | orange-red outside | all in all a bit darker | more red outside | yellow inside, red outside | orange inside, red outside more intensively | |
| Exp. 7.1; two heat treatments | yellow-orange | orange-red outside | all in all a bit darker | more red outside | yellow inside, red outside | orange inside, red outside more intensively | |
| Exp. 7.2; one heat treatment | light-light green | light-light green | light yellow inside, light blue outside | almost consistently light blue | consistently blue | no more change | |

TABLE 6-continued

| Combination | Time (hours) | | | | | |
|---|---|---|---|---|---|---|
| | immediately | 0.5 | 1 | 2 | 7 | 24 |
| Exp. 7.2; two heat treatments | light-light green | light-light green | light yellow inside, light blue outside | almost consistently light blue | consistently blue | no more change |
| Exp. 7.3; one heat treatment | light-light yellow | light-light yellow | light yellow | light yellow inside, green-blue outside | yellow inside, light blue otherwise | consistently blue |
| Exp. 7.3; two heat treatments | light-light yellow | light-light yellow | light yellow | light yellow inside, green-blue outside | light blue | consistently blue |
| Exp. 8.1; one heat treatment | yellow-orange | dark orange | red outside | red outside | dark orange inside, red outside | dark orange inside, red outside |
| Exp. 8.1; two heat treatments | yellow-orange | dark orange | red outside | red outside | dark orange inside, red outside | dark orange inside, red outside |
| Exp. 8.2; one heat treatment | light yellow | light yellow | green outside | green outside | light green | green-light blue |
| Exp. 8.2; two heat treatments | light yellow | light yellow | a bit green outside | a bit green outside | light green | light green |
| Exp. 8.3; one heat treatment | light yellow | light yellow | a bit greenish outside | a bit greenish outside | light green | green-light blue |
| Exp. 8.3; two heat treatments | light yellow | light yellow | a bit greenish outside | a bit green outside | light green | light green |

Even after a second sterilization, all tested oxygen indicators turn the respective color after a short time upon contact with oxygen. Thus, it is possible to recycle the oxygen indicators according to the invention.

The invention claimed is:

1. An oxygen indicator containing resorufin and/or toluidine blue as organic redox dye, glycerol, an organic or inorganic buffer, and water, incorporated into hydroxyethyl starches and/or methylcellulose and/or gelatin as auxiliary agents.

2. The oxygen indicator according to claim 1, characterized in that said buffer is a phosphate and/or citrate buffer.

3. The oxygen indicator according to claim 1, characterized in that said buffer is a phosphate and/or citrate buffer contained at a concentration of from 0.001 to 2 mol, based on the oxygen indicator.

4. The oxygen indicator according to claim 1, containing resorufin and having a pH within a range of from 6 to 10.

5. The oxygen indicator according to claim 1, containing toluidine blue and having a pH within a range of from 2 to 6.

6. The oxygen indicator according to claim 1, characterized in that methylcellulose, microcrystalline cellulose, lysine, lysine hydrochloride, magnesium stearate and/or silicones, especially gelatin and/or hydroxyethyl starches, are employed as further auxiliary agents.

7. The oxygen indicator according to claim 1, characterized by comprising a support material, especially an ion exchanger, paper or sheet.

8. The oxygen indicator according to claim 7, characterized in that said ion exchanger comprises a polymer-based anion or cation exchanger or a polymeric carbohydrate derivative.

9. The oxygen indicator according to claim 1, in the form of a tablet, capsule or gel, and/or placed into a separate outer packaging, preferably a bag or blister pack.

10. The oxygen indicator according to claim 1, characterized in that said redox dye is contained in its reduced form.

11. The oxygen indicator according to claim 10, characterized in that said redox dye is treated with a reducing agent having a higher reduction potential than that of the dye itself, especially glucose, sodium disulfite, zinc, $MnCl_2$, N-acetylcysteine and/or ascorbic acid.

12. The oxygen indicator according to claim 1, characterized in that the reduced form of the redox dye has protecting groups that will cleave off during a temperature treatment.

13. The oxygen indicator according to claim 12, characterized in that said protecting group contains a benzoyl group.

14. The oxygen indicator according to claim 1, characterized in that said redox dye is contained in its oxidized form and is subjected to reduction during a temperature treatment.

* * * * *